(12) United States Patent
Williams

(10) Patent No.: US 11,801,321 B2
(45) Date of Patent: Oct. 31, 2023

(54) SCENTED DECORATIVE PLUNGER HOLDER

(71) Applicant: Beleatha Joyce Williams, Fishkill, NY (US)

(72) Inventor: Beleatha Joyce Williams, Fishkill, NY (US)

(*) Notice: Subject to any disclaimer, the term of this patent is extended or adjusted under 35 U.S.C. 154(b) by 112 days.

(21) Appl. No.: 17/300,583

(22) Filed: Aug. 25, 2021

(65) Prior Publication Data

US 2023/0063520 A1 Mar. 2, 2023

(51) Int. Cl.
*A47K 17/00* (2006.01)
*A61L 9/01* (2006.01)

(52) U.S. Cl.
CPC .............. *A61L 9/01* (2013.01); *A47K 17/00* (2013.01)

(58) Field of Classification Search
CPC .. A61L 9/01; A47K 17/00; A47K 1/09; A46B 15/009; A46B 2200/304; A46B 2200/3046; E03C 1/308; A45D 44/18
USPC ................... 206/15.2, 361; 4/255.01, 255.12
See application file for complete search history.

(56) References Cited

U.S. PATENT DOCUMENTS

| | | | |
|---|---|---|---|
| 6,038,709 A * | 3/2000 | Kent ...................... | A47K 11/10 4/255.05 |
| 6,109,429 A * | 8/2000 | Cunningham .......... | A47K 17/00 206/823 |
| 7,841,029 B1 * | 11/2010 | Williams ............... | A47K 17/00 4/661 |
| 9,441,353 B1 * | 9/2016 | Hamil ..................... | E03D 11/00 |
| 2009/0095646 A1 * | 4/2009 | Reynolds ............... | A47K 17/00 206/361 |
| 2012/0267856 A1 * | 10/2012 | Swan ..................... | E03D 9/005 273/348 |

* cited by examiner

*Primary Examiner* — William V Gilbert

(57) ABSTRACT

The Scented Decorative Plunger Holder is a canister for holding a plunger. The holder has a lid and body. The lid has a portion configured to contain a scented agent, and this portion is magnetically connected to the lid. The lid and body have vents. The Scented Decorative Plunger Holder, can be made in a variety of styles using any color or a multi-color design.

1 Claim, 5 Drawing Sheets

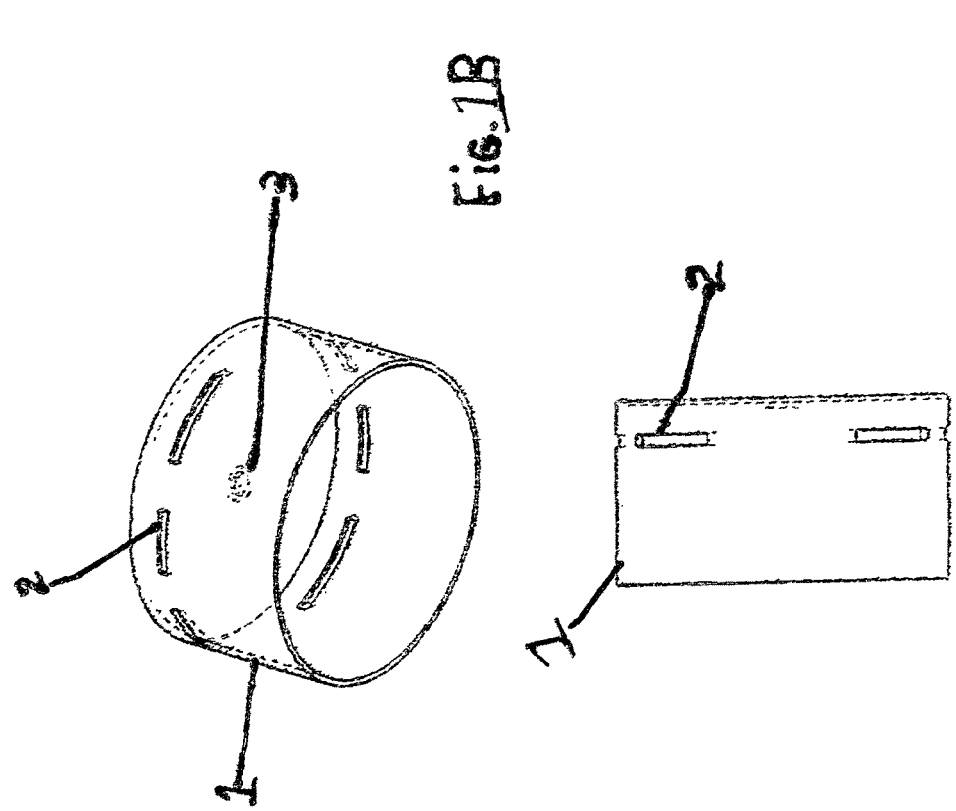
Fig. 1B
Fig. 1D
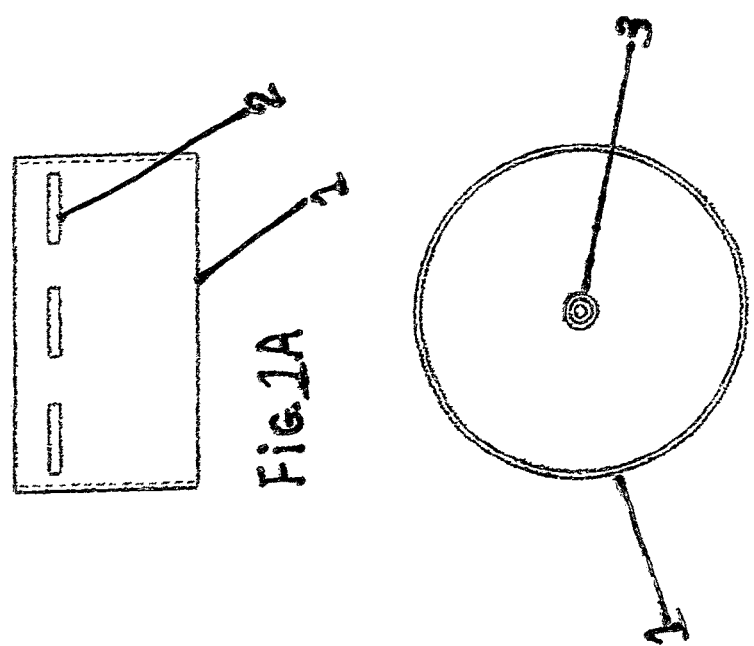
Fig. 1A
Fig. 1C

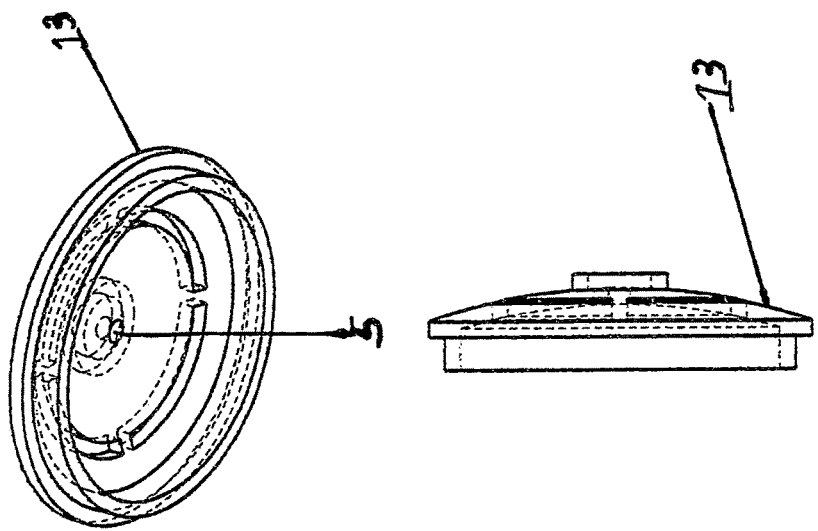
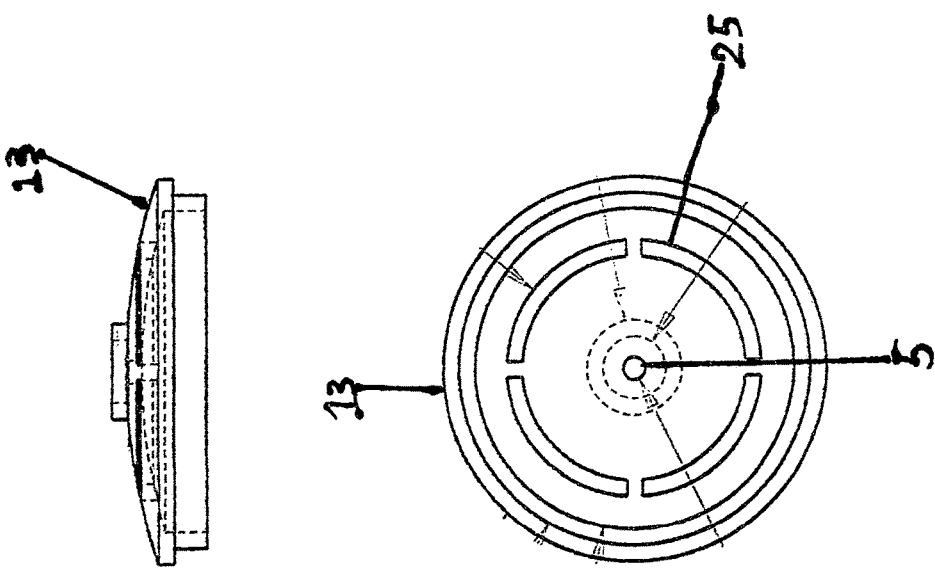

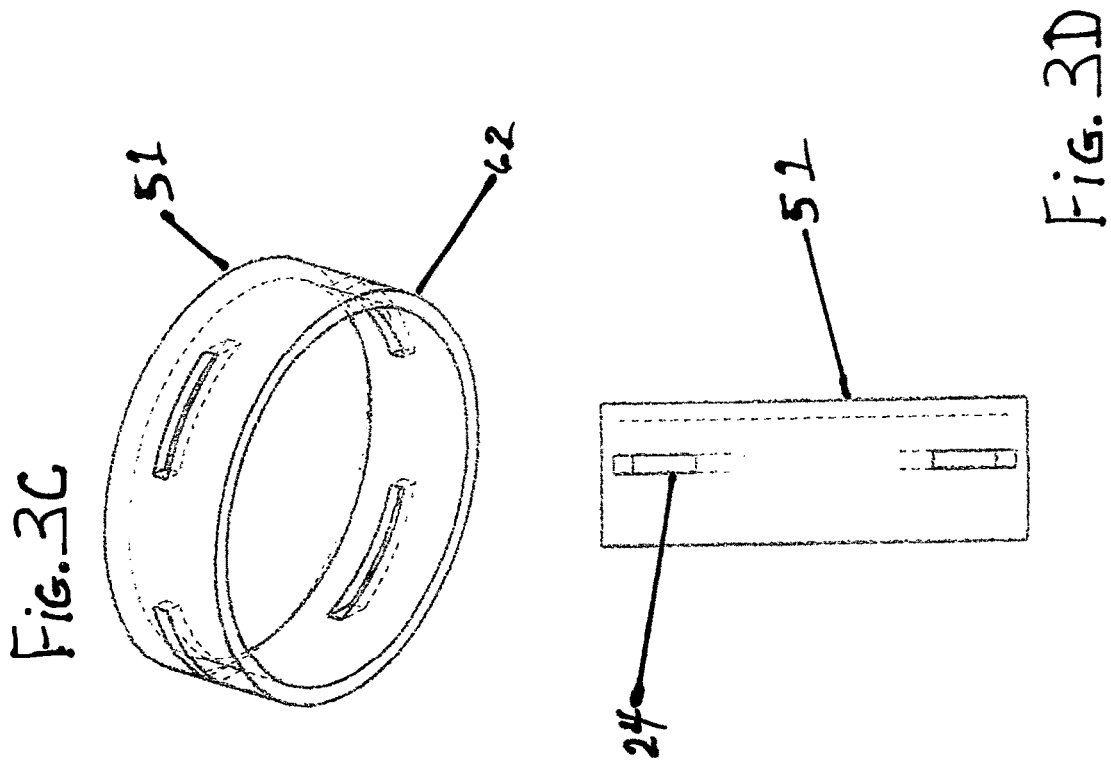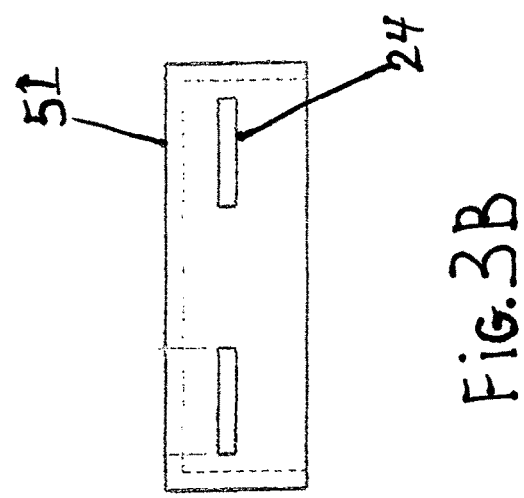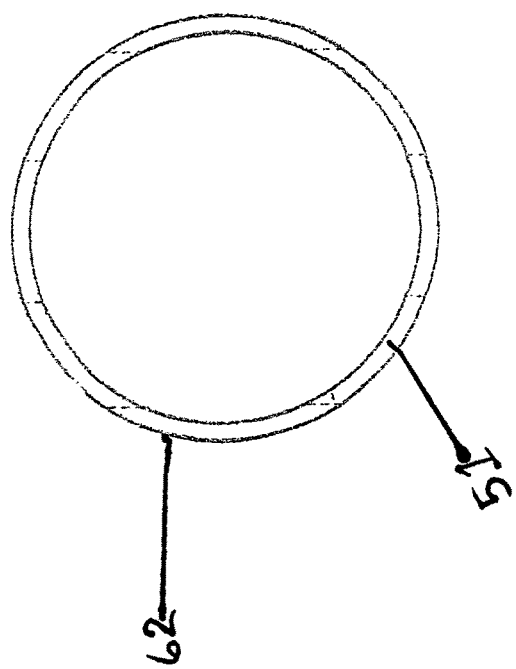

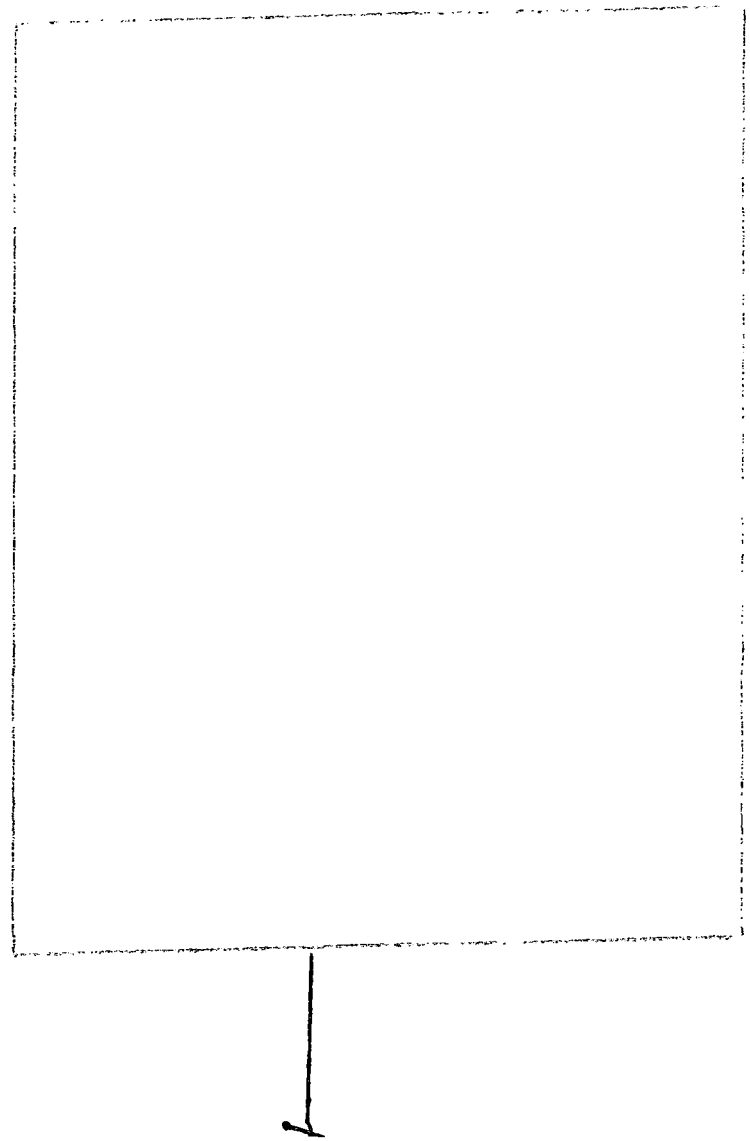
Fig. 5B
Fig. 5A

SCENTED DECORATIVE PLUNGER HOLDER

CROSS-REFERENCE TO RELATED APPLICATIONS

None

THE NAMES OF THE PARTIES TO A JOINT RESEARCH AGREEMENT

Not applicable

STATEMENT REGARDING PRIOR DISCLOSURES BY THE INVENTOR OR A JOINT INVENTOR

None

BRIEF DESCRIPTION OF THE SEVERAL VIEWS OF THE INVENTION

FIG. 1A through FIG. 1D are views of the lid of the present invention.

FIG. 2A through FIG. 2D are views of the fragrance reservoir of the present invention.

FIG. 3A through FIG. 3D are views of the bottom section of the present invention.

FIG. 5A and FIG. 5B are views of the sticker/decal of the present invention.

DETAILED DESCRIPTION OF THE INVENTION

Figure 4B:
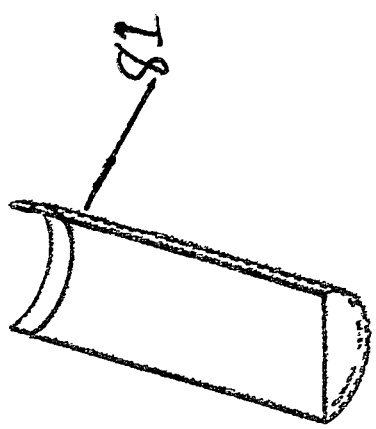
FIG. 4A through FIG. 4D are views of the cylinder-shaped case of the present invention.

FIG. 1A, FIG. 1B, FIG. 1C and FIG. 1D are components of the lid (1). The lid has vents (2), spaced about a perimeter surface of the lid to allow a freshener, as explained in FIG. 2A-FIG. 2D below, to freely escape. The lid also has a magnet (3) on an inner surface. This magnet secures the fragrance reservoir (FIG. 2A: 13) to the inside of the lid.

FIG. 2A, FIG. 2B, FIG. 2C and FIG. 2D show various views of the fragrance reservoir (13) of the present invention. The fragrance reservoir (13) contains a second magnet (5) configured to couple with the magnet (3) of the lid (1). The fragrance reservoir (13) also has spaced vents (25) configured to permit fragrance contained therein to escape.

The fragrance reservoir (13) can be removed by the coupled magnets (3 and 5) to permit replacement of the fragrance as desired.

FIG. 3A, FIG. 3B, FIG. 3C and FIG. 3D are components of the bottom section (51) of the fragrance reservoir (13). The bottom section (51) has a plurality of vents (24) spaced around the side portion (62). These vents (24) permit air flow from the inside to the outside of the fragrance reservoir (13). The bottom section (51) is removably connected to said fragrance reservoir (13).

Figure 4D:
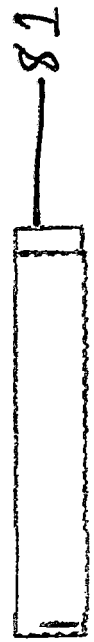
Figure 4A:
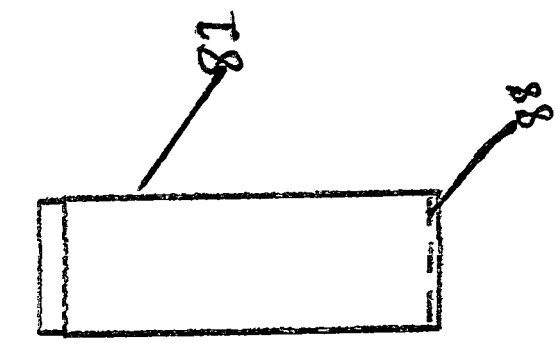
Figure 4C:

FIG. 4A, FIG. 4B, FIG. 4C and FIG. 4D as described are sections (81) forming the cylinder-shaped portion of the canister. Two sections of the cylinder (81) are assembled to form a cylindrical section of the canister. Each section (81) has a plurality of vents (88) spaced about a lower portion of the cylinder-shaped portion.

FIG. 5A and FIG. 5B provide an example of how the canister and lid can be decorated via a sticker or decal (84) that is configured to wrap around sections (81).

During assembly a canister is formed via sections (81) and the lid (1) is placed at a top portion of sections (81), The lid (1) has the fragrance reservoir (13) magnetically attached thereto via magnets (3) and (5), and the lid is located at a top portion of (81). The canister is configured to receive and contain a plunger therein.

The invention claimed is:

1. A scented plunger holder, comprising:
a lid, said lid having a first portion and a perimeter portion extending from said first portion, said perimeter portion having a first plurality of vents spaced about said perimeter portion, said lid having a first magnet on an inner surface of said first portion;
a fragrance reservoir having a second magnet attached thereto, said second magnet configured to mate with said first magnet to secure said fragrance reservoir to said lid, said fragrance reservoir having a second plurality of vents spaced about said fragrance reservoir;
a bottom section releasably connected to said fragrance reservoir, said bottom section having a third plurality of vents spaced about a side portion of said bottom section; and
a cylindrical portion having a first end configured to receive said lid and a second portion opposite said first portion, said cylindrical portion having a fourth plurality of vents spaced about a surface of said cylindrical portion proximate said second portion.

* * * * *